(12) United States Patent
Kuhr et al.

(10) Patent No.: US 7,396,334 B2
(45) Date of Patent: Jul. 8, 2008

(54) ANALYTICAL DEVICE WITH LANCET AND TEST ELEMENT

(75) Inventors: Hans-Juergen Kuhr, Mannheim (DE); Michael Fritz, Biblis (DE); Thomas Weiss, Mannheim (DE); Richard Forster, Pfreimd (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 230 days.

(21) Appl. No.: 10/230,851

(22) Filed: Aug. 29, 2002

(65) Prior Publication Data

US 2003/0050573 A1 Mar. 13, 2003

(30) Foreign Application Priority Data

Aug. 29, 2001 (DE) ................ 101 42 232

(51) Int. Cl.
*A61B 5/00* (2006.01)
(52) U.S. Cl. ....................... 600/583; 606/181
(58) Field of Classification Search ........ 606/167, 606/181, 182, 183; 600/583, 573, 576, 577, 600/578, 584
See application file for complete search history.

(56) References Cited

U.S. PATENT DOCUMENTS

| | | | |
|---|---|---|---|
| 4,398,544 A | | 8/1983 | Nugent et al. |
| 4,442,836 A | | 4/1984 | Meinecke et al. |
| 4,627,445 A | | 12/1986 | Garcia et al. |
| 4,660,570 A | * | 4/1987 | Dombrowski ........ 600/578 |
| 5,035,704 A | | 7/1991 | Lambert et al. |
| 5,122,123 A | | 6/1992 | Vaillancourt |

(Continued)

FOREIGN PATENT DOCUMENTS

DE 28 03 345 B1 6/1979

(Continued)

OTHER PUBLICATIONS

Surelets Stick it to the Competition/Surelet Blood Lancets . . . in a Class by Themselves, Product Brochure, , Gainor Medical, Long Beach, California, USA.

(Continued)

*Primary Examiner*—Michael J. Hayes
*Assistant Examiner*—Michael G. Mendoza
(74) *Attorney, Agent, or Firm*—Woodard, Emhardt, Moriarty, McNett & Henry LLP

(57) ABSTRACT

The invention concerns an analytical device containing a lancet comprising a lancet needle and a lancet body, the lancet needle being movable relative to the lancet body and the lancet body being composed, at least in the area of the tip of the lancet needle, of an elastic material in which the tip of the lancet needle is embedded, and an analytical test element which is permanently connected to the lancet body. In addition the invention concerns an analytical device containing a lancet comprising a lancet needle and a lancet body which is in the form of a hollow body in the area of the tip of the lancet needle and surrounds the tip of the lancet needle, the lancet needle being movable relative to the lancet body and the hollow body being composed at least partially of an elastic material, and an analytical test element which is permanently connected to the lancet body. Finally the invention concerns a process for manufacturing such an analytical device.

40 Claims, 6 Drawing Sheets

U.S. PATENT DOCUMENTS

| | | | |
|---|---|---|---|
| 5,231,993 A * | 8/1993 | Haber et al. ................ | 600/583 |
| 5,312,366 A | 5/1994 | Vaillancourt | |
| 5,358,489 A * | 10/1994 | Wyrick ....................... | 604/136 |
| 5,385,571 A | 1/1995 | Morita | |
| 5,514,152 A * | 5/1996 | Smith ......................... | 606/182 |
| 5,554,166 A | 9/1996 | Lange et al. | |
| 5,636,640 A | 6/1997 | Staehlin | |
| 5,662,127 A | 9/1997 | De Vaughn | |
| 5,779,677 A * | 7/1998 | Frezza ........................ | 604/134 |
| 5,801,057 A | 9/1998 | Smart et al. | |
| 5,871,494 A | 2/1999 | Simons et al. | |
| 5,879,311 A | 3/1999 | Duchon et al. | |
| 5,951,492 A | 9/1999 | Douglas et al. | |
| 6,014,577 A | 1/2000 | Henning et al. | |
| 6,032,059 A | 2/2000 | Henning et al. | |
| 6,036,924 A | 3/2000 | Simons et al. | |
| 6,048,352 A | 4/2000 | Douglas et al. | |
| 6,056,701 A | 5/2000 | Duchon et al. | |
| 6,099,484 A | 8/2000 | Douglas et al. | |
| 6,120,676 A | 9/2000 | Heller et al. | |
| 6,132,449 A | 10/2000 | Lum et al. | |
| 6,143,164 A | 11/2000 | Heller et al. | |
| 6,447,482 B1 * | 9/2002 | Rønborg et al. ............. | 604/131 |
| 6,472,220 B1 * | 10/2002 | Simons et al. ................ | 436/63 |
| 6,537,257 B1 * | 3/2003 | Wien .......................... | 604/198 |
| 6,561,989 B2 | 5/2003 | Whitson | |
| 6,612,111 B1 | 9/2003 | Hodges et al. | |
| 6,616,616 B2 | 9/2003 | Fritz et al. | |
| 6,706,159 B2 * | 3/2004 | Moerman et al. ...... | 204/403.03 |
| 6,783,502 B2 | 8/2004 | Orloff et al. | |
| 7,001,344 B2 * | 2/2006 | Freeman et al. ............. | 600/583 |
| 2002/0103499 A1 | 8/2002 | Perez et al. | |
| 2002/0177763 A1 | 11/2002 | Burns et al. | |
| 2003/0083685 A1 | 5/2003 | Freeman et al. | |
| 2003/0083686 A1 | 5/2003 | Freeman et al. | |
| 2003/0144608 A1 | 7/2003 | Kojima et al. | |
| 2003/0153939 A1 | 8/2003 | Fritz et al. | |
| 2003/0212344 A1 | 11/2003 | Yuzhakov et al. | |
| 2004/0034318 A1 | 2/2004 | Fritz et al. | |

FOREIGN PATENT DOCUMENTS

| | | |
|---|---|---|
| EP | 0199484 | 6/1985 |
| EP | 0359831 | 3/1990 |
| EP | 0565970 B1 | 6/1994 |
| EP | 0931507 A1 | 7/1999 |
| EP | 1 466 558 A2 | 8/2002 |
| GB | 2 331 936 A1 | 6/1999 |
| JP | 2000-116626 | 4/2000 |
| WO | WO 9848695 | 11/1998 |
| WO | WO 9929429 | 6/1999 |
| WO | WO 9926539 | 10/1999 |
| WO | WO 01/66010 A1 | 3/2000 |
| WO | WO 00/40150 | 7/2000 |

OTHER PUBLICATIONS

SURELITE . . . lancets that baby your skin, Packaging and Ordering Information, , Gainor Medical, Long Beach, California, USA.

* cited by examiner

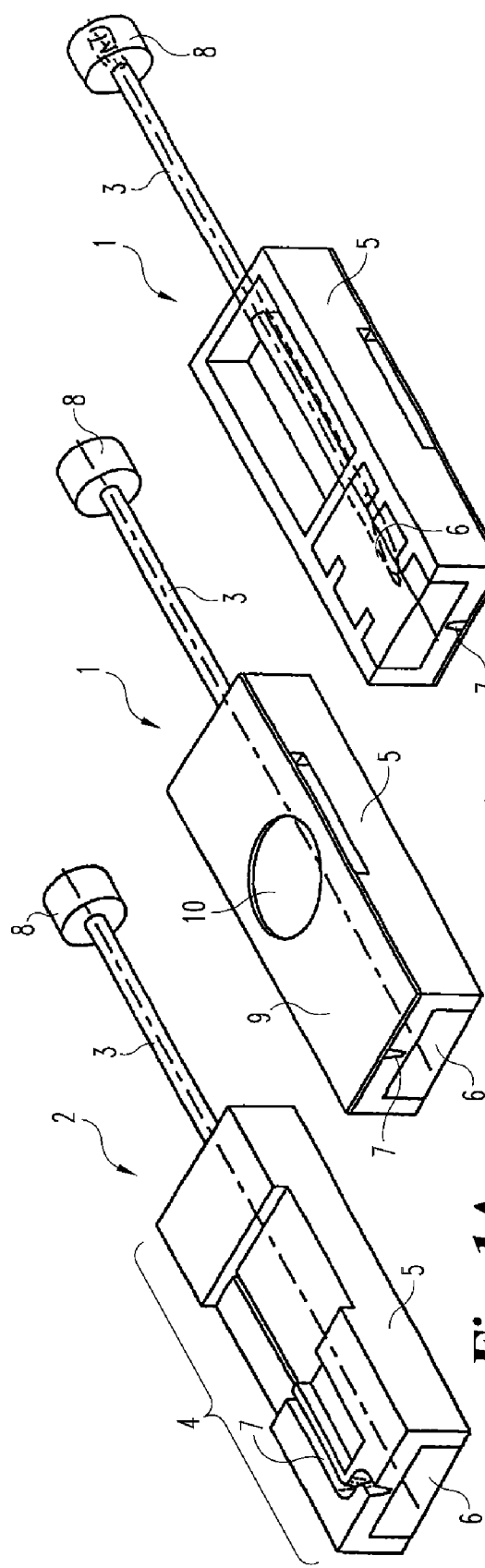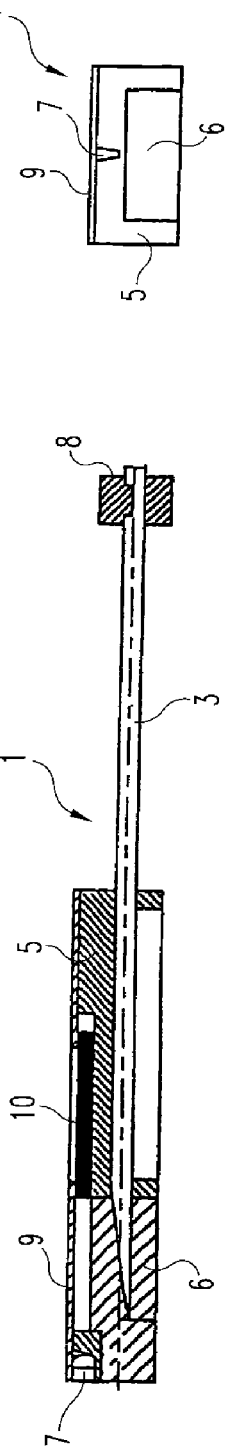

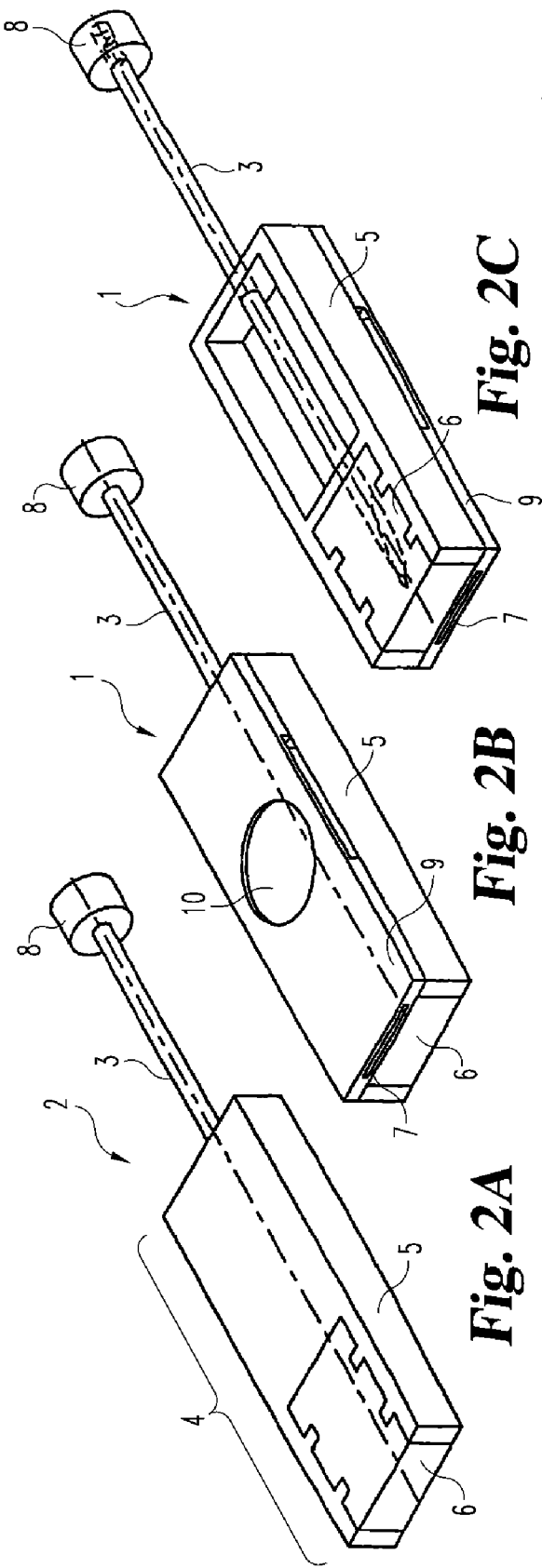

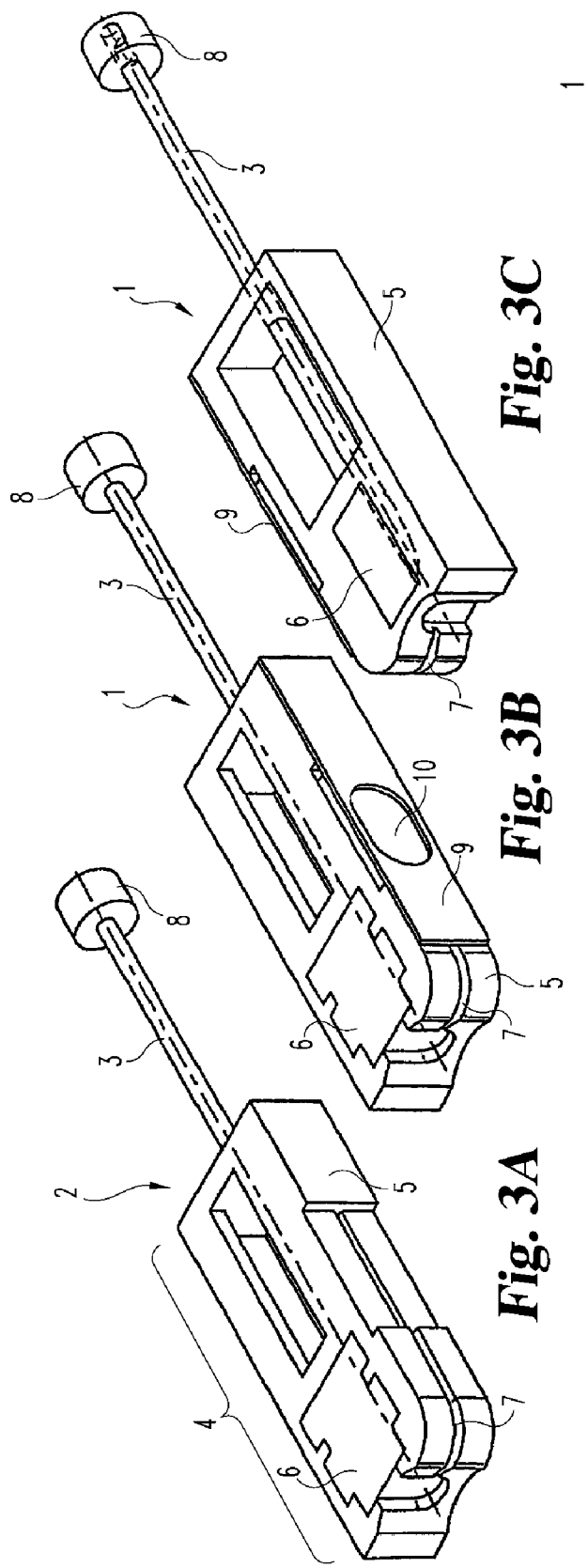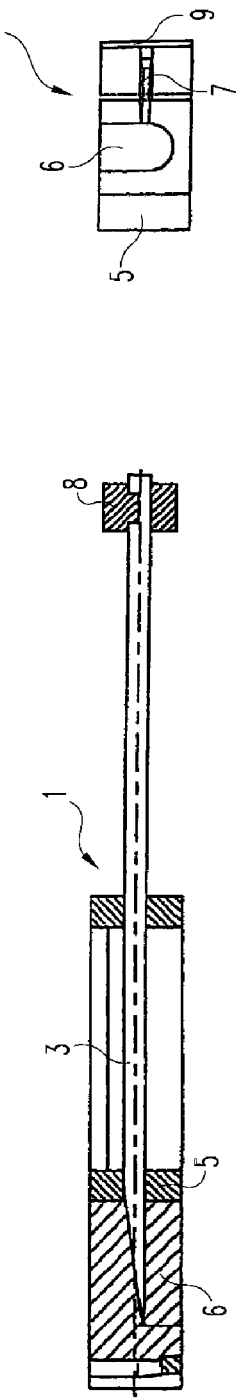

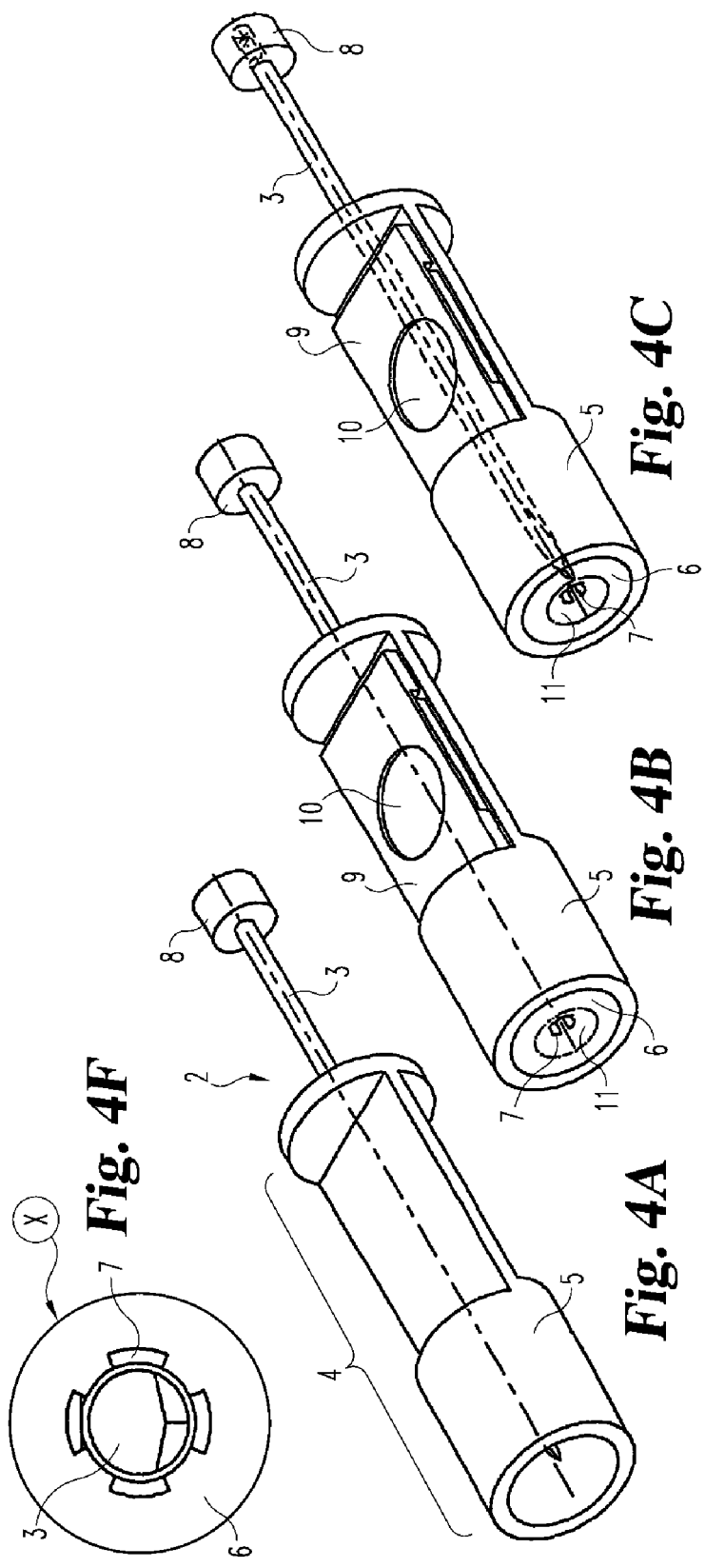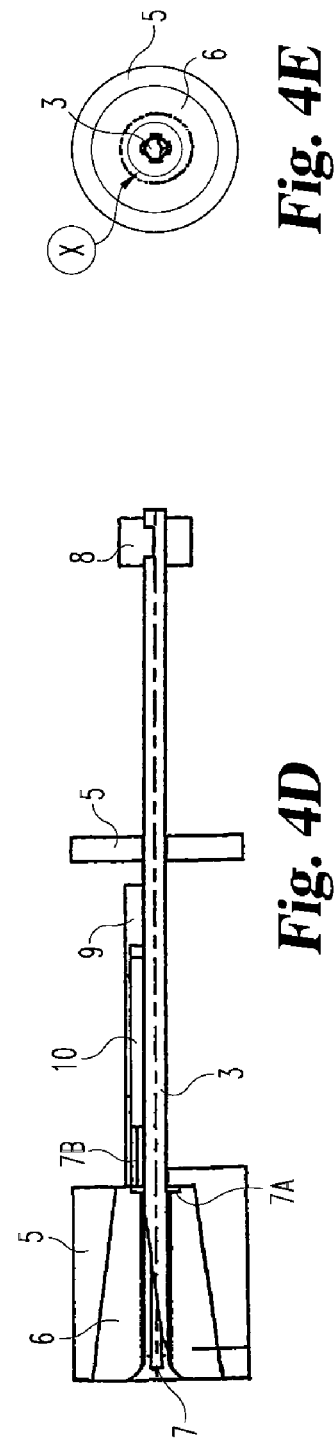

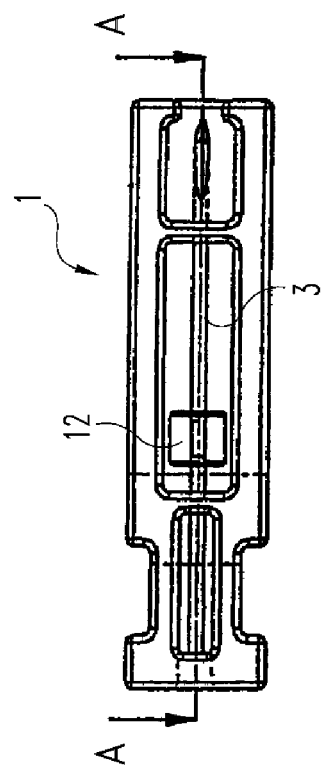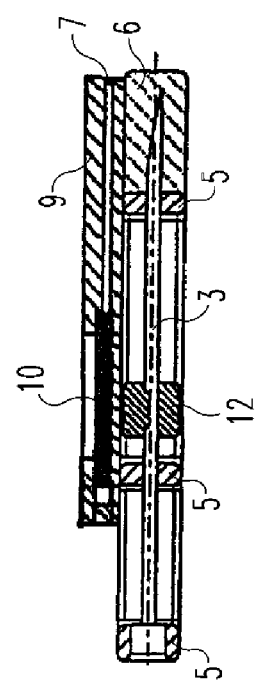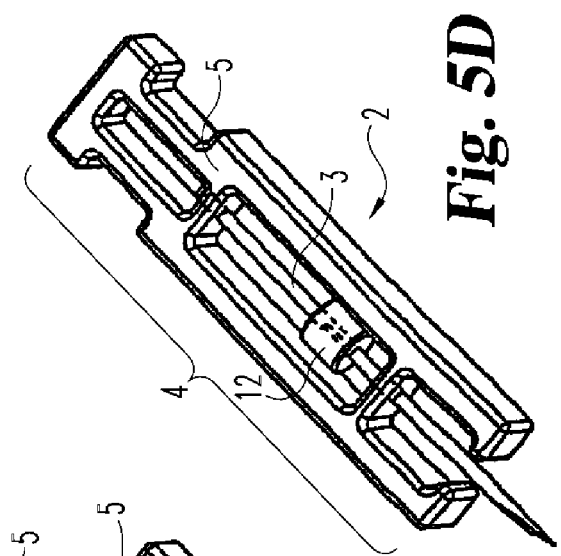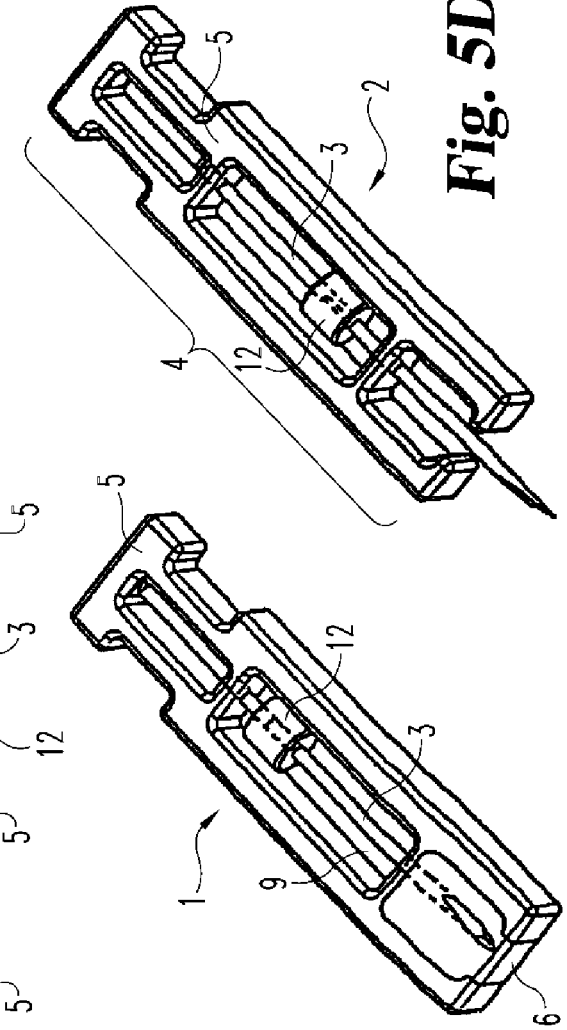
Fig. 5A
Fig. 5B
Fig. 5D
Fig. 5C

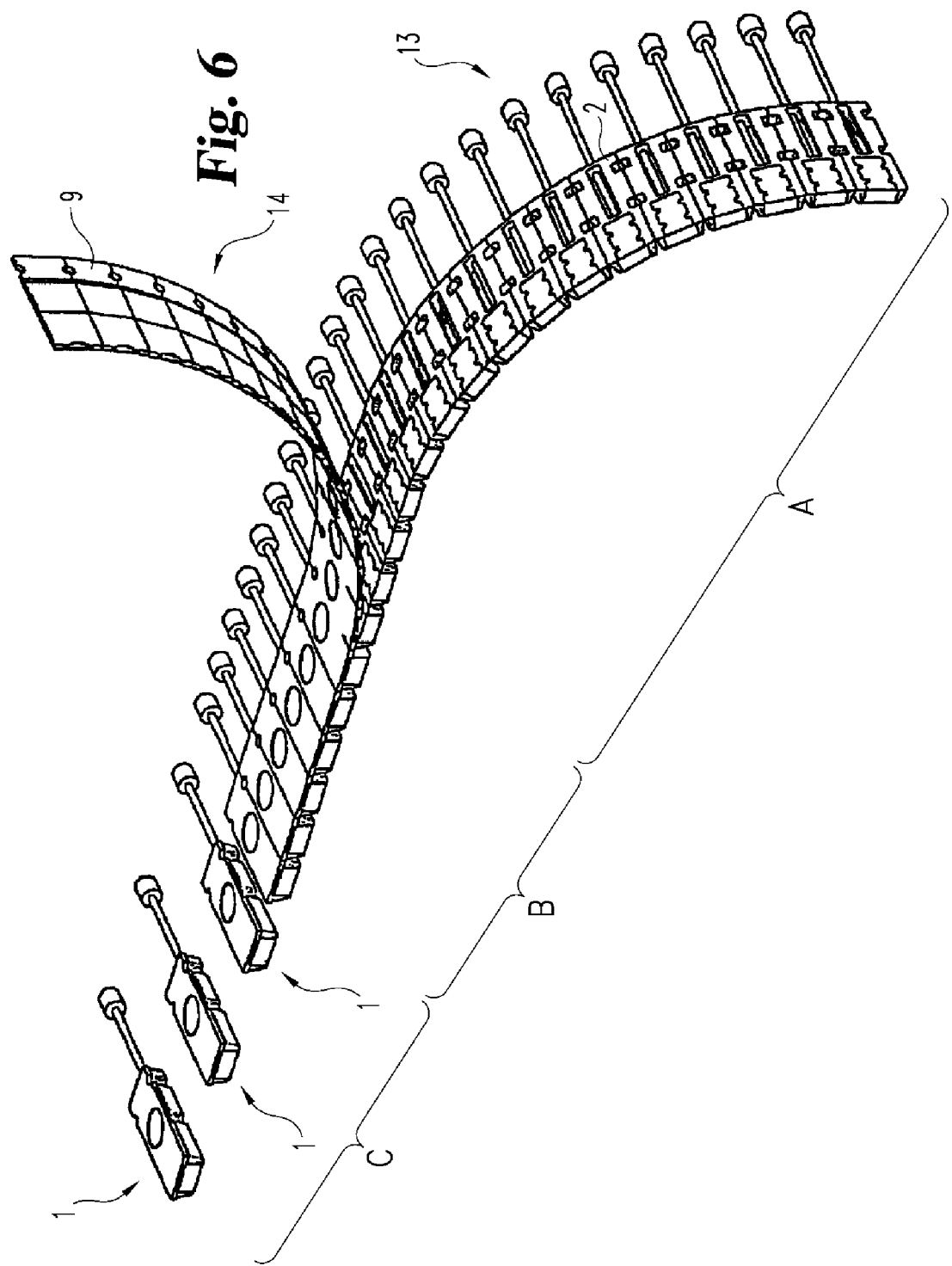

ANALYTICAL DEVICE WITH LANCET AND TEST ELEMENT

The invention concerns an analytical device which contains a lancet and an analytical test element. The invention also concerns a process for manufacturing such an analytical device.

The examination of blood samples in clinical diagnostics enables the early and reliable recognition of pathological states as well as a specific and well-founded monitoring of physical conditions. Medical blood diagnostics always requires the collection of a blood sample from the individual to be examined. Whereas in hospitals and in doctor's offices several millilitres of blood are usually collected by venepuncture from a person to be examined for analysis in order to carry out many laboratory tests, individual analyses which are directed towards one parameter nowadays often only require blood quantities ranging from a few microlitres down to less than one microlitre. Such small quantities of blood do not require a laborious and painful venepuncture. Instead it is sufficient to push a sterile sharp lancet into a finger pad or earlobe of the person to be examined to collect blood through the skin and thus to obtain a few microlitres of blood or less for analysis. This method is particularly suitable when it is possible to carry out the analysis of the blood sample immediately after blood collection.

Lancets and suitable instruments for them (so-called blood withdrawal instruments, blood lancet devices or—as they are referred to in the following—lancing aids) which enable blood collection that is as painfree and reproducible as possible are available especially for so-called home monitoring i.e. where medical laymen carry out simple analyses of the blood by themselves and are used in particular by diabetics to collect blood regularly and several times daily to monitor the blood glucose concentration. Furthermore the use of lancets with lancing aids is intended to reduce the psychological barrier associated with piercing one's own body which is particularly important for children that suffer from diabetes and need regular blood glucose tests. The commercially available instruments (lancing aids) and lancets Glucolet® from Bayer AG and Softclix® from Roche Diagnostics GmbH are mentioned as examples of lancets and lancing aids. Such lancets and instruments (lancing aids) are for example the subject matter of WO-A 98/48695, EP-A 0 565 970, U.S. Pat. No. 4,442,836 or U.S. Pat. No. 5,554,166.

Personal blood sugar determination (so-called home monitoring) is today a world-wide method in diabetes monitoring. Blood sugar instruments of the prior art such as the Accu-Chek Sensor (from Roche Diagnostics) are composed of a measuring instrument into which a test element (test strip, sensor) is inserted. The test strip is contacted with a drop of blood which has previously been collected from the finger pad by means of a lancing aid. The numerous system components (lancet, lancing aid, test strip and measuring instrument) need a lot of space and require a relatively complex handling. There are now also systems with a high degree of integration which are thus more simple to operate. These for example include the AccuCheck Compact (from Roche Diagnostics), the Glucometer Dex (from Bayer Diagnostics) and the Soft-Sense (from Medisense). In the two former systems the test strips are stored in the measuring instrument in magazines and are available for the measurement.

A next step in miniaturization is for example to integrate several functions or functional elements into a single analytical device (disposable). For example the operating process can be considerably simplified by a suitable combination of the lancing process and sensory analyte concentration detection on a test strip. There are the following examples of this in the prior art:

EP-B 0 199 484 (Audio Bionics) describes an analytical device ("disposable"; abbreviated dispo) containing an integrated lancet which is actuated by the instrument (see FIG. 9 for example). The lancet is retracted again after the puncture by means of a specific spring mounting ("spring-mounted lance means"). The dispo contains a so-called "wick means" through which the sample liquid is passed from the body surface to the analytical area which is an optically analysable test field.

A method is described in U.S. Pat. No. 6,143,164 (E. Heller & Comp.) in which a body opening (for example a small puncture or incision through the skin) is made and subsequently body fluid is transported into a sensor and examined there for the presence of an analyte. For this purpose U.S. Pat. No. 6,143,164 discloses an analytical device in which a lancing device is attached to a sensor test strip. The sample liquid is transported from the body opening to the actual detection element of the sensor for example again by means of a wick or a capillary gap/channel.

WO 99/26539 (Mercury Diagnostics), U.S. Pat. No. 5,951,492 (Mercury Diagnostics) and U.S. Pat. No. 6,056,701 (Amira Medical) describe, inter alia, collection devices for body fluids comprising an elongate handle; a test field being attached to its head region.

U.S. Pat. No. 6,032,059 (Abbott) and U.S. Pat. No. 6,014,577 (Abbott) describe a disposable containing a needle which is used to pierce the skin. Body fluid which is previously sucked into the needle by capillary action is analysed by a sensor integrated into the needle.

U.S. Pat. No. 5,801,057 (Smart et al.) describes a disposable made of silicon containing an integrated hollow needle. A collection chamber for aspirated body fluid is located at one end of this hollow needle. The concentration of a blood component can be determined in the body fluid by a suitable reaction chemistry.

U.S. Pat. No. 5,035,704 (Lambert et al.) discloses a system for collecting blood containing a magazine for disposables. It is possible to integrate a lancet element into the dispos. A blood drop is transferred to the test field by direct skin contact and can be increased by applying a vacuum.

U.S. Pat. No. 6,132,449 (Agilent Technologies) discloses an integrated dispo with a puncturing and measuring function. The puncturing element is activated perpendicular to the dispo plane whereby it passes through the dispo. The wound opening is in direct contact with several capillary structures which transport the emerging blood into a separate analytical part of the dispo.

A key problem in collecting blood using a so-called "integrated disposable" (in which the lancet and test element are connected together or form a single unit) is the fact that, after puncture, the capillary blood usually does not automatically emerge from the wound. This adverse effect is increased by directly contacting a disposable with the wound opening. After a puncture the blood drop must be actively conveyed to the skin surface by for example mechanically opening the wound and/or applying gentle pressure to the tissue around the wound area (for example by simple "finger milking"). Application of a vacuum can assist this process.

Experiments in the laboratory have shown that it is advantageous to keep the wound open during the period of blood collection. However, this fact results in a complicated movement process of the dispo since a very rapid piercing motion and a slow blood withdrawal movement can only be achieved with a waiting time in the system. Only a few of the dispo designs proposed in the prior art are suitable for this.

A rigid protruding lancet tip has a tendency to cause unintentional injury when collecting the blood drop. Hence a lancing device which moves relative to the disposable is preferable. However, this requirement in combination with the dispos known in the prior art leads to a complicated and thus expensive dispo design.

A further difficulty with known dispos is to ensure the sterility of the lancet for the period until it is used. In the prior art it is known that the tip can be protected by a cap which is manually removed before use. However, such a cap impairs the automation of blood sugar measurements. Previously described concepts which would in principle enable an automated blood sugar determination with an integrated disposable have the disadvantage that there is a latent risk of contaminating the lancet needle tip. Components of the test field (chemicals, biological components, adhesives etc.) can migrate within the dispo via the air or over the surfaces. Thus a sterilization of the needle tip carried out initially is in no way sufficient without further protective measures to meet the requirements for a sterile medical product.

The lancets of the prior art usually have a metal lancet needle with a tip which can be optionally ground. In order to facilitate the handling of the lancet and optionally to attach it in a lancing device, a plastic lancet body made of a rigid, injection-mouldable material is usually injected onto the lancet needle in many embodiments. In the unused state the tip of the lancet needle is surrounded by a protective covering to ensure its sterility. This is usually composed of the same rigid material as the actual lancet body and usually forms one unit with this body. The protective covering can be separated from the lancet body before using the lancet and removed from the tip of the lancet needle. For this purpose there is usually a weakened point between the lancet body and protective cover. After the lancet has been used, the tip of the lancet needle is unprotected and is hence a potential source of injury to the user and possibly to other persons.

The object of the present invention was therefore to eliminate the disadvantages of the prior art and in particular the disadvantages mentioned above. In particular the object of the present invention was to provide analytical devices (synonymous with "disposables", abbreviated: "dispos") which do not have the disadvantages of the prior art. In particular the dispo according to the invention should ensure the sterility of the lancets until they have been used while simultaneously integrating the lancet and test element (test strip, sensor). Of course it is also intended to describe a manufacturing process for such analytical devices. Another object of the present invention is to provide analytical devices containing lancets in which at least the lancet needle tip is kept sterile, i.e. germ-free, in the unused state until immediately before use and which can be stored hygienically in the used state. This object should be ideally achieved without the user having to employ separate measures for the hygienic storage. Moreover the user should be protected from accidental injury by the lancet and in particular by the used lancet. Finally it should be preferably possible to simply transfer the sample from the site of blood collection to the site of blood examination.

This object is achieved by the subject matter of the invention as characterized in the individual patent claims. Preferred embodiments are the subject matter of the dependent claims.

A first subject matter of the invention is an analytical device which contains a lancet. The main components of the lancet are a lancet needle with a tip and a lancet body that completely surrounds the lancet needle at least in the region of the tip. The lancet needle can be moved relative to the lancet body. The lancet body is composed of an elastic material at least in the region of the tip of the lancet needle in which the tip of the lancet needle is embedded. The analytical device additionally contains an analytical test element which is permanently attached to the lancet body.

Another subject matter of the invention is a further analytical device which contains a lancet. The lancet in this case comprises a lancet needle with a tip and a lancet body which is in the form of a hollow body in the region of the tip of the lancet needle and which surrounds the tip of the lancet needle. In this case the lancet needle is also movable relative to the lancet body. The hollow body is composed at least partially of an elastic material which can be pierced by the tip of the lancet needle during the lancing process and after retraction optionally reseals the tip of the lancet needle in the hollow body. The analytical device additionally contains an analytical test element which is permanently connected to the lancet body.

Finally the invention concerns a process for manufacturing such analytical devices.

The object of the invention is preferably composed of a miniaturized dispo which combines the three functions of puncturing, blood transfer from the wound generated by the puncturing to the test element and sensor in one element.

The main body of the analytical device according to the invention is composed of a rigid plastic body whose external shape is preferably adapted for the purpose of holding it in an instrument. A lancet needle is embedded in this plastic in such a manner that its tip preferably does not protrude beyond the front edge of the main body. The main body can therefore also be referred to as the lancet body. In the preferred embodiment the main body has ridges which are used to fix the needle in the main body and to guide it during the lancing movement. However, most of the needle is preferably not attached to the main body in order to reduce the frictional force during the lancing movement. The contact surfaces between the needle and lancet body are preferably kept to a minimum and suitably pretreated, for example siliconized.

The lancets according to the invention are preferably designed to be used once and can therefore be referred to as single-use blood lancets or disposable blood lancets. The lancet of the invention comprises a needle (lancet needle) with a tip. The needle is usually several millimetres (mm) to a few centimetres (cm) in length and has an elongate shape. Needles are typically cylindrical since this needle shape is particularly easy to manufacture; however, other needle shapes are also possible. The tip region of the needle comprises the needle tip which is inserted into the tissue when the lancet is used correctly. Consequently the tip of the lancet needle is that part of the lancet which comes into contact with the skin of the individual to be pricked which optionally injures the skin and thus causes a body fluid and in particular blood or interstitial fluid to flow out.

The tip of the lancet needle can for example be rotationally symmetrical which is generally the case for pins. However, it has also proven to be advantageous to provide the needle tip with one or several ground surfaces. The resulting edges which make an angle with the longitudinal axis of the needle and converge in a tip act as a sharp cutting edge during lancing and make the puncturing process less painful than is the case with rotationally symmetrical needles.

The lancet needle of the lancet according to the invention is manufactured from a material which is sufficiently rigid to withstand mechanical strain during the lancing process, the processing steps or other strains which may occur without deformation. The material must also be such that no particles break off or become detached during the lancing process.

Finally the needle material must also be sufficiently machinable to enable the needle tip to be sufficiently pointed and the edges of the needle to be ground adequately sharply. Very suitable materials for the lancet needle are above all metals and in particular high-grade steels. However, needles can also conceivably be made of silicon, ceramics or plastics. High-grade steel needles are particularly preferred.

In one embodiment of the invention at least the tip of the lancet needle of the lancet according to the invention is surrounded by the lancet body. In this connection it is important that the lancet body is composed of an elastic material in the region of the tip of the lancet needle. At least the tip of the lancet needle is completely surrounded on all sides by this elastic material i.e. it is embedded in it and thus sealed from the environment. The elastic material of the lancet body, which in the various embodiments can completely or only partially form the lancet body, is characterized in that it is soft, deformable and can be pierced by the tip of the lancet needle without damaging the tip. During the lancing process the lancet needle is moved along its longitudinal axis relative to the lancet body and its tip emerges from the lancet body in order to pierce the skin of the individual to be examined for blood collection. A further important and preferred property according to the invention is that the elastic material optionally again makes a tight seal around the tip of the lancet needle when the lancet needle is retracted into the lancet body. After the lancing process the lancet needle is moved in a preferred embodiment into its initial position relative to the lancet body by reversing the movement of the lancing process and in this position the tip is again completely enclosed on all sides by the elastic material of the lancet body.

The elastic material of the lancet body which completely encloses the tip of the lancet needle ensures the sterility of the lancet needle tip before use, preferably until immediately before use and optionally ensures a hygienic enclosure of the lancet needle tip after use. The term "hygienic enclosure" means that biological material (tissue, body fluid) which may adhere to the needle after the puncture is essentially encapsulated by the elastic material. This prevents especially germs and infectious material from reaching the environment or at least greatly reduces this risk. Consequently the elastic material is impervious to germs and thus prevents their penetration or escape depending on whether the lancet needle is unused or used. In addition the elastic material represents a mechanical protection for the lancet needle tip and thus also prevents accidental injury on the lancet needle tip.

Rubber, coautchouc, silicone, elastomers and in particular thermoplastic elastomers have proven to be suitable as an elastic material for the lancet body of the present invention. These have properties that are important for the present invention: they are soft, deformable, can be pierced by the lancet needle without damaging the tip and make a tight seal around the used lancet needle tip. Furthermore they can be used for injection moulding processes which allows a mass production of lancets in large numbers.

Thermoplastic elastomers which are also called elastoplasts or thermoplasts or thermoplastic coautchoucs ideally combine the handling properties of elastomers and the processing properties of thermoplasts. Thermoplastic elastomers are for example styrene oligoblock copolymers (so-called TPE-S), thermoplastic polyolefins (TPE-O), thermoplastic polyurethanes (TPE-U), thermoplastic copolyesters (TPE-E) and thermoplastic copolyamides (TPE-A). In particular thermoplastic elastomers based on styrene-ethylene-butylene-styrene-polymers (SEBS polymers, e.g. Evoprene® from Evode Plastics or Thermolast K from "Gummiwerk Kraiburg GmbH) have for example proven to be particularly suitable.

During the lancing process the lancet needle is moved relative to the lancet body. The latter is preferably held in its position by the lancing aid or lancing instrument during this process. The lancet needle can be specially shaped for the purposes of the drive mechanism and for example have a needle head at the end opposite to the tip or have another lancet body in addition to the lancet body which encloses the tip and can be engaged by a drive element of the lancing aid.

The shape of the needle or of the additional lancet body can interact in a suitable manner with a corresponding drive device in the lancing instrument (lancing aid). Such means can generally be referred to as a thickening of the needle.

In order to achieve the advantage that the lancet needle tip is enclosed in a sterile manner before use by the elastic material of the lancet body and is hygienically surrounded by the elastic material after use, it is of course necessary that the lancet needle is moved back after use, i.e. after the lancing process, essentially into its original position relative to the lancet body containing the elastic material. This can be achieved by suitable interaction with a correspondingly adapted lancing aid. It is only important that, after use, the lancet needle tip is again enclosed by the elastic material of the lancet body which thus prevents accidental injury on the needle tip.

In order to increase the stability of the elastic material it is possible to combine it with a stiff material, for example a stiff plastic material. For example the outside of the elastic material which does not come into contact with the tip of the lancet needle can be stabilized with a layer of a stiff material, for example a stiff plastic. It is also possible to manufacture the lancet body from elastic material only in the region of the lancet needle tip and to manufacture the remaining lancet body from conventional stiff plastics. In this case the elastic material and the stiff material can be glued together or joined together by an injection moulding process, for example a two component injection moulding process. The stiff material of the lancet body ensures the mechanical stability of the elastic material during the lancing process and facilitates the immobilization of the elastic part of the lancet body during the lancing process by the lancing aid. The stiff material can also be a part of the test element, for example a capillary gap test element as described in WO 99/29429.

In a further embodiment of the invention the lancet contains a lancet needle with a tip and a hollow body which surrounds at least the tip of the lancet needle, the lancet needle being movable within the hollow body in the region of its tip and the hollow body being at least partially composed of an elastic material that can be pierced by the tip of the lancet needle during the lancing process and which optionally reseals the tip of the lancet needle in the hollow body when it is retracted.

Whereas with the lancet described further above according to the first embodiment, the region of the tip of the lancet needle is completely surrounded on all sides by an elastic material and thus without any remaining hollow space around the tip to ensure sterility before use and hygienic shielding after use, in the second embodiment described above the tip of the lancet needle is surrounded by the hollow body which is closed on all sides. The areas of this hollow body which do not come into contact with the lancet needle are preferably manufactured from a stiff material and preferably an injection mouldable material. It is important for the invention that the area of the hollow body which is pierced by the lancet needle tip during the lancing process is composed of an elastic material.

During the lancing process the lancet needle is moved relative to the hollow body which represents the lancet body.

The holder and drive for the lancet needle and attachment of the lancet body can be achieved by suitable constructional measures in the lancing aid as described above.

The elastic material which comprises a part of the hollow lancet body is pierced by the lancet needle tip during the lancing process and optionally reseals after the lancet needle tip is retracted into the hollow body and thus seals the hollow body. Hence the lancet needle tip is thus aseptically sealed in the hollow body immediately before use and is hygienically enclosed in it after use.

The lancet of this embodiment can, like the lancet of the alternative inventive embodiment described above, also have an additional lancet body in addition to the lancet body which encloses the tip of the lancet needle which interacts with suitable elements of a lancing device during the lancing process. In addition the lancet needle can have a special shape, for example have a head at the end opposite to the tip.

With regard to the properties of the elastic material and the joining of the elastic material with the stiff material of the lancet body the same applies as that already mentioned above with reference to the first embodiment.

The blood transfer from the wound/puncturing site of the lancet to the measuring site is achieved according to the invention by two basically different methods: On the one hand the operator of the analytical device can manually transfer the blood drop obtained after the lancing process onto the corresponding test element. However, the blood transfer is preferably achieved "automatically" without any assistance by the user of the dispos according to the invention. For this purpose the dispo can have means for sample liquid transport. These means are preferably capillary active, for example in the form of a gap or a channel in a rigid main body or absorbent matrix materials. It is also possible to combine these two basic methods for example in that the blood is firstly transported through a capillary channel, taken up by an absorbent matrix material and dispensed onto a test element.

Fleeces, papers, wicks or fabrics have proven to be particularly suitable as absorbent materials in the sense of this invention.

In a preferred embodiment the main body (lancet body) of the analytical device contains the means for sample liquid transport. This may be an absorbent wick recessed into the lancet body or preferably a formed capillary gap which is located directly next to the needle and has an inlet in the proximity of the needle outlet. As a result the dispo does not have to be laterally moved for blood collection (or only slightly). The geometry of the inlet opening is designed such that the blood drop that forms can collect there as easily as possible and has for example a funnel or notch shape. The capillary action then ensures that the required amount of blood, which can be considerably below 1 microlitre, is aspirated. By this means the blood reaches the test field and reacts there with the test chemistry to generate an analysable electrical signal or colour change. The capillary gap can be moulded into the plastic during the injection moulding or be subsequently introduced into the plastic body for example by embossing or milling.

In another preferred variant the means for sample liquid transport (e.g. a capillary gap or a wick) is not moulded into the plastic which forms the lancet body but is produced by the specific structure of the test element. For example the test element can have a structure similar to WO 99/29429 or EP-A 0 359 831.

The methods known in the prior art are used for the sensory detection of the analyte in particular of blood glucose. Photometric and electrochemical methods are preferred.

The analytical test element of the inventive analytical device can be composed of a detection film which is directly joined to the lancet body. Such detection films are known in diverse embodiments from the prior art. For example such a detection film is described in WO 99/29429. Furthermore, as already mentioned above, a complete conventional test element can be joined to the main body/lancet body of the device according to the invention. Such test elements are also known to a person skilled in the art.

The test element can be joined to the lancet body in many different ways. These include but are not limited to, glueing, welding, clipping, attachment via velcro fastening or magnets, sewing, screwing and such like. The test element is preferably glued to the lancet body for example by means of hot-melt adhesive or by means of a double-coated adhesive tape.

In general the operation of the disposables according to the invention can be described as follows:
1. The dispo is inserted into the holding device of a (blood sugar) measuring instrument and is attached there.
2. The drive mechanism of the lancing unit is tensioned and coupled to the needle thickening of the dispo.
3. When the lancing process is actuated, the needle is moved forwards and in this process emerges at high speed from the soft plastic. The entire lancing process only takes a few milliseconds.
4. After the skin has been punctured the needle is retracted again into the soft plastic (initial position). The drive is optionally disengaged.
5. After a suitable drop of blood has formed, the entire collection device is moved forward until the suction opening (e.g. capillary) contacts the drop. Alternatively the blood drop can be manually applied to the appropriate sample application zone of the test element.
6. In the variants of the disposable which have means for sample liquid transport, the suction action of these means transports the blood in the dispo to a site where a signal is generated by means of a photometric or electrochemical reaction which depends on the concentration of the blood component.

A disposable according to the invention can in principle be manufactured by the following simple steps:
(1) Injection moulding the main body including embedding the lancet needle (optionally with generation of the "needle head" i.e. a thickening that can be engaged by a lancing instrument)
(2) sheathing the needle tip with soft plastic
(3) sterilizing the "crude disposables" (which are essentially composed of the lancet optionally together with a capillary channel in the lancet body) for example by means of gamma radiation
(4) test assembly i.e. connecting the test element with the main body.

Preferably the "crude dispos" as well as the test elements can be present as a tape material which is separated into the individual dispos after the test assembly for example by cutting or punching. Irrespective of whether the disposables according to the invention are manufactured as rolls or tape material in a continuous process or batch-wise or individually, it is important that the lancet and test element are not joined together until after the lancet needle has been sterilized. A sterilization of the-disposables after final assembly could result in damage to sensitive chemical or biological substances in the test field. This can be avoided by the process according to the invention.

Finally a subject matter of the invention is the use of an elastic material as a component of a lancet of an analytical device where the elastic material maintains the sterility of at least the tip of a lancet needle in the unused state. In a preferred embodiment the elastic material can also be used to hygienically shield at least the tip of the lancet needle in the used state.

The use according to the invention of an elastic material to shield the tip of the lancet needle ensures the sterility of an unused lancet needle tip and optionally hygienically shields the used lancet needle tip.

The lancet needle tip can be sterilized in the unused state by suitable measures such as for example gamma radiation. Once sterilized the lancet needle tips remain sterilized by the corresponding lancet body which includes an elastic material. In contrast to the prior art where no elastic materials for shielding lancet needle tips have been described, the use of the elastic material according to the invention also enables the hygienic screening or shielding of the used lancet needle tip. The use of the elastic material allows resealing of a channel which may be present for a brief time through which the lancet needle can pass for the purposes of lancing after the lancet needle has been retracted i.e. after completion of the lancing process. Hence contaminants, in particular germs and infectious material which may adhere to the lancet needle tip after the lancing process cannot reach the environment or only to a limited extent. This is of particular advantage for disposable lancets which are individually disposed of after use. This property is, however, of outstanding importance for sets of lancets and lancet magazines in which used lancets are stored next to unused lancets which can then be disposed of as a whole.

The invention has the following advantages:

The tip of the lancet needle is shielded germ-tight in the unused state in all embodiments i.e. germs cannot reach the lancet needle tip until immediately before using the lancet. After suitable sterilization the lancet tips remain sterile for a long period.

The sterility of the lancet needle is also ensured in the subsequent manufacturing steps such as the joining of lancet and test element. In this process the sensitive needle tip is protected from mechanical influence (bending etc.).

In all embodiments the tip of the lancet needle can be hygienically screened in the used state. An accidental contamination of the surroundings (user, objects, other lancets) is substantially excluded.

The user of disposables according to the invention is protected from accidental injury on a used lancet needle. The same of course also applies to other persons than the actual user.

The disposables according to the invention can be manufactured cost-effectively in large numbers using conventional injection moulding processes.

The disposables according to the invention can be miniaturized to a substantial degree and are therefore suitable for use in compact automated systems.

All previously known variants of test strips and sensors can be used as analytical test elements.

The invention is further elucidated by the following figures:

FIG. 1 shows schematically a first preferred embodiment of the analytical device according to the invention in several views.

FIG. 2 shows schematically a second preferred embodiment of the analytical device according to the invention in several views.

FIG. 3 shows schematically a third preferred embodiment of the analytical device according to the invention in several views.

FIG. 4 shows schematically a fourth preferred embodiment of the analytical device according to the invention in several views.

FIG. 5 shows schematically a fifth preferred embodiment of the analytical device according to the invention in several views.

FIG. 6 shows schematically the manufacture of analytical devices according to FIG. 2 from tape material.

Although only test elements that can be evaluated optically are shown in each of the individual figures, this should not be limiting to the subject matter of the present invention. Rather it is obvious to a person skilled in the art that the detection reaction of the test element can be monitored by any method. In addition to optical methods (such as reflection photometry, absorption measurement or fluorescence measurement) in particular electrochemical methods are preferred (such as potentiometry, amperometry, voltametry, coulometry for example).

The figures and letters in the figures denote:
1 analytical device (disposable, dispo)
2 lancet
3 lancet needle
4 lancet body
5 plastic part of the lancet body
6 part of the lancet body made of elastic material
7 capillary gap
8 thickening of the needle end
9 test element
10 test field
11 sealing foil
12 thickening in the middle of the needle
13 lancet tape/belt
14 test element tape/belt FIG. 1 shows schematically a preferred embodiment of the analytical device in several detail figures (1A-1E).

FIG. 1A firstly shows the lancet (2). It contains a lancet needle (3) which is embedded in a lancet body (4). The lancet body (4) is composed of a hard plastic part (5) and a part made of elastic material (6). A capillary gap (7) is worked into the hard plastic part (5) of the lancet body (4) and is used to transport the sample liquid.

A thickening (8) is attached to the rear end of the lancet needle (3) and enables the lancet needle to be easily gripped in the lancing aid or in the lancing instrument.

FIG. 1B shows the final analytical device (1). A strip-shaped test element (9) which contains a test field (10) is attached to the hard plastic part (5) of the lancet body (4). The test field is accessible for sample liquid through the capillary gap (7).

FIG. 1C shows a perspective view of the underside of the analytical device (1). In this view it is clear that the hard plastic part (5) of the lancet body (4) only touches and holds the lancet needle (3) in the area of two bars. Furthermore the dashed lines indicate how the tip of the lancet needle (3) is embedded in the elastic material (6) of the lancet body.

FIG. 1D shows a longitudinal section through the analytical device (1).

FIG. 1E shows a front view of the analytical device (1).

The drawings (2A-2E) of FIG. 2 show another preferred embodiment of the analytical device according to the invention.

In FIG. 2A the lancet (2) of the analytical device (1) is first shown in perspective from above. The lancet (2) is composed of a lancet needle (3) which is embedded in a lancet body (4).

This is composed of a hard plastic part (5) and a part made of an elastic material (6). In addition a thickening (8) is attached to the rear end of the lancet A needle (3) which is used to grip the lancet needle (3) by a lancing instrument.

In contrast to FIG. 1 the analytical device in FIG. 2 does not have a capillary gap in the lancet body (4) but as part of the test element (9).

FIG. 2B shows the final assembled analytical device (1) in which a test element (9) is attached to the lancet body (4). This test element contains a capillary gap (7) which makes the test field (10) accessible to a blood sample.

FIG. 2C shows a perspective view of the analytical device (1) according to FIG. 2B from below. As in FIG. 1C, FIG. 2C makes it clear that the lancet needle (3) is only connected to the hard plastic part (5) of the lancet body (4) by bars. The needle tip of the lancet needle (3) is completely embedded in the elastic material (6) of the lancet body.

FIG. 2D represents a longitudinal section through the analytical device (1) of FIG. 2B. FIG. 2E shows a corresponding front view of the analytical device (1) of FIG. 2B. FIGS. 2D and 2E make it clear that the capillary gap (7) is port of the test element (9).

FIG. 3 shows another preferred embodiment of the analytical device (1) of the invention in several detailed drawings (3A-3E).

The embodiment of FIG. 3 contains a capillary gap (7) as part of the hard plastic part (5) of the lancet body (4) similar to the embodiment of FIG. 1. Only the position of the capillary gap (7) and the position of the test element (9) differ from the embodiment of FIG. 1. Whereas in the embodiment of FIG. 1 the test element (9) and capillary gap (7) are arranged on one of the large boundary surfaces of the lancet body (4), these elements are arranged laterally on one of the narrow boundary surfaces of the lancet body (4) in the embodiment of FIG. 3. Otherwise the function and structure of the embodiment of FIG. 3 essentially corresponds to that described in FIG. 1. In this connection FIGS. 3A to 3E correspond to FIGS. 1A to 1E.

Another preferred embodiment of the analytical device (1) according to the invention is shown in several detailed drawings (FIGS. 4A-4F) in FIG. 4. Whereas in the embodiments according to FIG. 1 to FIG. 3 the capillary gap (7) was either part of the hard plastic part (5) of the lancet body (4) or part of the test element (9), the capillary gap (7) in the embodiment of FIG. 4 is partially disposed in the elastic material (6) of the lancet body (4) and partially in the test element (9). As shown in particular in FIG. 4D the capillary gap (7) can be divided into three partial regions (7, 7A and 7B). These are in contact with one another in such a manner that sample liquid transport is possible.

As in the embodiments of FIGS. 1 to 3, the embodiment of FIG. 4 is composed of a lancet (2) which contains a lancet needle (3) which is partially surrounded by a lancet body (4). In this case the lancet body (4) is composed of a hard plastic part (5) and an elastic material (6) which in particular surrounds the lancet needle tip (cf. FIG. 4A). A thickening (8) is attached to the lancet needle at the rear end of the lancet body (3) which in turn is designed to enable a lancing device to grip the needle (3).

As shown in FIGS. 4B and 4C, a test element (9) which contains a test field (10) is attached to the lancet body (4). As already described the test field (10) is accessible to the sample liquid via a system of capillary channels (7, 7A, 7B).

The outlet opening of the lancet needle (3) is closed by a sealing foil (11) in this embodiment. When the lancet is used the sealing foil (11) can either be pierced by the lancet needle (3) or the sealing foil (11) is removed manually before use.

FIG. 4E shows a front view of the outlet opening of the lancet of the analytical device (1).

FIG. 4F shows an enlarged view of the detail labelled X in the front view of FIG. 4E. This view shows especially that four capillary channels (7) which enable sample transport to the test element (9) are present in the elastic material (6) of the lancet body (4).

A thickening (8) is provided in the rear of the lancet needle (3) in embodiments of FIGS. 1 to 4 which is of major importance for the lancing movement. This thickening (8) is designed such that it can be coupled to a lancing drive. In this case the drive carries out the forwards and backwards movement of the needle (3). Alternatively a drive coupling is also conceivable in which a plunger carries out the forward movement. It is then moved back by a spring which is pressed together during the forward movement and then subsequently relaxes. The thickening (8) on the needle (3) is important for this as one of the contact points for the spring. This spring can either be a component of the disposable or a component of the instrument or of a cassette or a magazine. The thickening (8) can for example be an attachable plastic or metal part. The needle (3) can also be mechanically deformed (squeezing, bending) to produce a thickening (8).

Another embodiment of the invention is shown in several detailed drawings (5A-5D) of FIG. 5. In this embodiment the thickening (11) of the lancet needle (3) is not at the rear end of the lancet needle (3), but rather in the region of the middle of the needle. In this case the thickening is located inside the lancet body (4). In this case an appropriate drive mechanism can only act laterally on the disposable. An advantage of this solution is that disposables are particularly compact and robust.

Otherwise the analytical device (1) corresponds essentially to the embodiment of FIG. 2.

Of course it is also possible to combine an embodiment of FIG. 1 i.e. an embodiment in which the capillary gap (7) is part of the lancet body (4) with a thickening (12) in the middle of the needle.

FIG. 5A shows a view of the analytical device (1) from below. FIG. 5B shows a sectional view through the longitudinal axis of the analytical device (1). FIG. 5C shows a perspective view of the underside of the analytical device (1) in which the lancet needle (3) is in a position in which it is before or after the lancing process. The tip of the lancet needle is embedded in the elastic material (6) of the lancet body. In FIG. 5D—which for the sake of clarity is shown without a test element (9) and elastic material (6)—the lancet (2) is in the position in which the lancet needle (3) is present during the lancing process. The lancet needle tip protrudes from the contours of the lancet body (4).

FIG. 6 is a greatly simplified schematic representation of how analytical devices (1) according to FIG. 2 are manufactured from tape material. In area A lancets (12) which are assembled to form a tape or belt (13) and test elements (9) are assembled to form a tape or belt (14). Two tapes are combined in area B and the test element tape (14) is glued to the lancet tape (13). Finally in area C the combined tapes are cut into individual analytical devices (1) for example by cutting off the terminal device (1).

The invention claimed is:
1. Analytical device containing
   i) a lancet comprising
      a lancet needle with a tip and
      a lancet body which is in the form of a hollow body in the area of the tip of the lancet needle and which surrounds the tip of the lancet needle, the lancet needle being movable relative to the lancet body and the hollow body being composed at least partially of a material that can be pierced by the tip of the lancet needle during the lancing process, wherein the material that can be pierced is a thermoplastic elastomer; and ii) an analytical test element configured to detect analyte the analytical test element being permanently connected to the lancet body.

2. Analytical device as claimed in claim 1, characterized in that the lancet body has means for sample liquid transport.

3. Analytical device as claimed in claim 1, characterized in that the test element has means for sample liquid transport.

4. Analytical device as claimed in claim 2, characterized in that the means for sample liquid transport is a capillary gap, a capillary channel or a wick or a bar made of an absorbent material.

5. Analytical device as claimed in claim 2, characterized in that the means for sample liquid transport has a sample application site which is directly adjacent to the position where the lancet needle extends from the lancet body to cut tissue.

6. Process for manufacturing an analytical device as claimed in claim 1, wherein
a lancet is prepared
the lancet needle is sterilized and
subsequently the analytical test element is permanently connected to the lancet body.

7. An analytical device, comprising:
a body,
a lancet needle having at least a tip embedded in the body to maintain the sterility of the tip before use,
the body including material that is pierceable by the lancing tip to form a temporary channel that allows movement of the tip to a extended position where the tip extends from the body to cut tissue,
the tip of the lancet being moveable relative to the body between the extended position and a retracted position where the tip is located inside the material, and
a test element joined to the body for testing of analyte in body fluid from the cut.

8. The device of claim 7, further comprising means for transporting the body fluid to the test element.

9. The analytical device of claim 7, wherein the analytical device has a capillary gap to transport the body fluid to the test element.

10. An apparatus, comprising:
an analytical device comprising
a body,
a lancet needle having at least a tip embedded in the body to maintain the sterility of the tip before use,
the body including material that is pierceable by the lancing tip to form a temporary channel that allows movement of the tip to a extended position where the tip extends from the body to cut tissue,
the tip of the lancet being moveable relative to the body between the extended position and a retracted position where the tip is located inside the material, and
a test element joined to the body for testing of analyte in body fluid from the cut;
a body fluid measuring instrument having a lancet drive mechanism coupled to the analytical device, the drive mechanism being configured to move the tip of the lancet needle between the extended and the retracted position; and
the analytical device being configured to be removed from the instrument after use and replaced with a new one.

11. The apparatus of claim 10, further comprising a tape that includes plurality of the analytical devices joined together.

12. The apparatus of claim 11, further comprising:
a first belt that includes a plurality of the lancet needles; and
a second belt that includes a plurality of the elements, wherein the second belt is joined to the first belt.

13. An analytical device, comprising:
a body,
a lancet needle having at least a tip embedded in the body to maintain the sterility of the tip before use,
the body including material that is pierceable by the lancing tip to form a temporary channel that allows movement of the tip to a extended position where the tip extends from the body to cut tissue,
the tip of the lancet being moveable relative to the body between the extended position and a retracted position where the tip is located inside the material,
a test element joined to the body for testing of analyte in body fluid from the cut;
wherein the analytical device has a capillary gap to transport the body fluid to the test element; and
wherein the capillary gap is defined at least in part by the body.

14. The device of claim 13, wherein the capillary gap is defined between the body and the test element.

15. The device of claim 13, wherein the capillary gap is defined between the body and the lancet needle.

16. An analytical device, comprising:
a body,
a lancet needle having at least a tip embedded in the body to maintain the sterility of the tip before use,
the body including material that is pierceable by the lancing tip to form a temporary channel that allows movement of the tip to a extended position where the tip extends from the body to cut tissue,
the tip of the lancet being moveable relative to the body between the extended position and a retracted position where the tip is located inside the material,
a test element joined to the body for testing body fluid from the cut;
a plurality of the analytical devices incorporated into a magazine; and
wherein the material minimizes contamination between used and unused ones of the analytical devices in the magazine.

17. The device of claim 16, wherein the magazine is configured for disposal of the plurality of the analytical devices as a whole.

18. An analytical device, comprising:
a body;
a lancet needle having at least a tip embedded in the body to maintain the sterility of the tip before use;
the body including material that is pierceable by the lancing tip to form a temporary channel that allows movement of the tip to a extended position where the tip extends from the body to cut tissue;
the tip of the lancet being moveable relative to the body between the extended position and a retracted position where the tip is located inside the material;
a test element joined to the body for testing of analyte in body fluid from the cut; and
wherein the material includes an elastic material to reseal the channel when the tip returns to the retracted position after the tissue is cut to encapsulate the tip after use.

19. The device of claim 18, wherein the elastic material includes a thermoplastic elastomer.

20. The device of claim 18, wherein the body includes a stiff material joined to the elastic material to stabilize the elastic material during lancing.

21. The device of claim 20, wherein the stiff material includes a stiff plastic.

22. The device of claim 18, wherein the test element includes a stiff material to stabilize the elastic material during lancing.

23. An apparatus, comprising:
a first belt that includes a plurality of lancets, each of the lancets having at least a lancet tip embedded in the first belt to maintain sterility of the lancet tip before use, wherein the first belt is pierceable by the lancet tip of each of the lancets to allow extension of the lancet tip from the first belt to cut an incision in tissue and to allow retraction back inside the first belt after cutting the incision; and
a second belt that includes a plurality of test elements for analyzing body fluid from the incision, wherein the second belt is joined to the first belt.

24. The apparatus of claim 23, wherein the first belt and the second belt are glued together.

25. The apparatus of claim 23, further comprising:
means for cutting the incision, wherein the means for cutting the incision includes the lancets; and
means for analyzing the body fluid, wherein the means for analyzing the body fluid includes the test elements.

26. An analytical device, comprising:
a body;
a lancet having at least lancet tip embedded in the body to maintain sterility of the lancet tip prior to use, the lancet tip being configured to pierce the body when extending from the body during lancing an incision;
wherein the body is configured to hygienically enclose the lancet tip when the lancet tip retracts inside the body after lancing; and
a test element fixed to the body for analyzing analyte in body fluid from the incision.

27. The analytical device of claim 26,
wherein the lancet has an initial position in which at least the lancet tip is embedded in the body to maintain sterility of the lancet tip until immediately before use and an extended position at which the lancet tip extends from the body to create the incision;
wherein the lancet is moveable to return to the initial position after creating the incision to minimize risk of injury; and
wherein the body is pierceable by the lancet tip to allow movement of the lancet to the extended position.

28. The analytical device of claim 26, wherein the body defines a capillary channel that is fixed relative to the body for drawing the body fluid from the incision to the test element.

29. The analytical device of claim 26, wherein:
the body is configured to allow the lancet to be sterilized separately from the test element to prevent contaminants from the test element migrating onto the lancet; and
at least a portion of the body is made of material that is able to be pierced by the lancet tip during lancing to promote automatic body fluid analysis by eliminating manual cap removal from the lancet.

30. The analytical device of claim 26, further comprising:
means for lancing the incision, wherein the means for lancing the incision includes the lancet;
means for maintaining sterility of the lancet tip prior to use, wherein the means for maintaining the sterility includes the body; and
means for analyzing the body fluid, wherein the means for analyzing the body fluid includes the test element.

31. An analytical device, comprising:
a body;
a lancet having at least lancet tip embedded in the body to maintain sterility of the lancet tip prior to use, the lancet tip being configured to pierce the body when extending from the body during lancing an incision;
wherein the body is configured to hygienically enclose the lancet tip when the lancet tip retracts inside the body after lancing;
a test element fixed to the body for analyzing analyte in body fluid from the incision;
wherein the body has at least a portion made of elastic material that is configured to be pierced by the lancet during lancing; and
a stiff material attached to the elastic material to ensure mechanical stability of the elastic material during lancing.

32. The analytical device of claim 31, wherein the body includes the stiff material.

33. The analytical device of claim 31, wherein the test element includes the stiff material.

34. An apparatus, comprising:
a magazine;
a plurality of analytical devices housed in the magazine; and
wherein each of the analytical devices includes
a lancet for creating an incision in tissue,
a body in which at least a portion of the lancet is embedded for maintaining sterility of the lancet prior to creating the incision, wherein the body is able to pieced by the lancet,
a test element coupled to the body for analyzing fluid from the incision, and
wherein the body is configured to encapsulate the lancet after creating the incision to minimize cross-contamination between the used and unused analytical devices in the magazine.

35. The apparatus of claim 34, wherein the magazine is configured to allow disposal of the plurality of the analytical devices at the same time.

36. The apparatus of claim 34, further comprising:
means for creating the incision, wherein the means for creating the incision includes the lancet;
means for maintaining sterility of the lancet prior to creating the incision, wherein the means for maintaining sterility includes the body; and
means for analyzing the fluid from the incision, wherein the means for analyzing the fluid includes the test element.

37. An apparatus, comprising:
an analytical device comprising
a test element configured to analyze analyte in body fluid,
a lancet having a lancet tip configured to pierce tissue to supply the body fluid to the test element,
a body attached to the test element,
at least the lancet tip being sealed inside the body, wherein the body isolates the lancet tip from the test element to allow the lancet to be sterilized separately from the test element, and
the body being pierceable by the lancing tip to permit movement of the lancet tip to an extended position where the lancet tip pierces the tissue.

38. The apparatus of claim 37, further comprising:
a body fluid measuring instrument having a lancet drive mechanism coupled to the analytical device, the drive mechanism being configured to move the lancet tip of the lancet between the extended position and a retracted position; and the analytical device being configured to be removed from the instrument after use and replaced with a new one.

39. The apparatus of claim 37, further comprising:
a first belt that includes a plurality of the lancets; and
a second belt that includes a plurality of the test elements, wherein the second belt is joined to the first belt.

40. The apparatus of claim 37, further comprising:
a magazine;
a plurality of the analytical device incorporated into the magazine; and
wherein the body of the analytical device minimizes cross-contamination inside the magazine.

* * * * *

UNITED STATES PATENT AND TRADEMARK OFFICE
CERTIFICATE OF CORRECTION

PATENT NO.       : 7,396,334 B2
APPLICATION NO.  : 10/230851
DATED            : August 29, 2002
INVENTOR(S)      : Hans-Juergen Kuhr Page 1 of 1

It is certified that error appears in the above-identified patent and that said Letters Patent is hereby corrected as shown below:

Column 16, line 32 claim 34, replace "to pieced" with --to be pierced--

Signed and Sealed this

Ninth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,396,334 B2 Page 1 of 1
APPLICATION NO. : 10/230851
DATED : July 8, 2008
INVENTOR(S) : Hans-Juergen Kuhr It is certified that error appears in the above-identified patent and that said Letters Patent is hereby corrected as shown below:

Column 16, line 32 claim 34, replace "to pieced" with --to be pierced--

This certificate supersedes the Certificate of Correction issued September 9, 2008.

Signed and Sealed this

Thirtieth Day of September, 2008

JON W. DUDAS
*Director of the United States Patent and Trademark Office*